United States Patent [19]

Harata

[11] Patent Number: 5,550,632
[45] Date of Patent: Aug. 27, 1996

[54] METHOD FOR EVALUATING GLOSS AND BRIGHTNESS CHARACTER OF COATED PAINT FILM

[76] Inventor: Hiroaki Harata, No. 1-20-22, Daido, Kanazawa-ku, Yokohama City, Kanagawa Pref., Japan

[21] Appl. No.: 714,542

[22] Filed: Jun. 13, 1991

[30] Foreign Application Priority Data

Jun. 20, 1990 [JP] Japan ................................. 2-159860

[51] Int. Cl.⁶ .................................................. G01N 21/32
[52] U.S. Cl. ...................... 356/446; 356/371; 356/124.5
[58] Field of Search .................................. 356/445, 446, 356/448, 124.5, 371

[56] References Cited

U.S. PATENT DOCUMENTS

| 4,846,578 | 7/1989 | Morita et al. | 356/446 |
| 5,092,676 | 3/1992 | Harata et al. | 356/371 |

FOREIGN PATENT DOCUMENTS

| 58-97608 | 6/1983 | Japan. |
| 61-217708 | 9/1986 | Japan. |
| 63-274847 | 11/1988 | Japan. |
| 1-210806 | 8/1989 | Japan. |
| 1-210807 | 8/1989 | Japan. |
| 1-213509 | 8/1989 | Japan. |

OTHER PUBLICATIONS

German PTO Office Action, Dated Sep. 14, 1992, Application No. P 41 20 289.9–52.

Primary Examiner—Hoa Q. Pham

[57] ABSTRACT

A method for evaluating the gloss and brightness character of a coated paint film. The method is comprised of projecting a brightness and darkness pattern onto the surface of the coated paint film. The projected pattern is picked up by a CCD camera and converted to a two-dimensional brightness and darkness pattern image. The disturbance of the pattern image is separated into a plurality of spatial frequency ranges. Each of the spatial frequency ranges is independently quantified to obtain an evaluation value which is in close correlation to a corresponding organoleptic evaluation value based on human's visual observation.

12 Claims, 4 Drawing Sheets

METHOD FOR EVALUATING GLOSS AND BRIGHTNESS CHARACTER OF COATED PAINT FILM

BACKGROUND OF THE INVENTION

1. Field of the Invention

This invention relates to a method for evaluating a gloss and brightness character of a coated paint film, and more particularly to such a method for obtaining numerically estimated values representing the gloss and brightness character, with the numerical having good correlation to corresponding organoleptic values.

2. Description of the Prior Art

It has been well confirmed from a variety of studies, that unevenness of the surface of a coated paint film is a composite wave compound of a variety of waves having frequencies ranging from several μm to several cm. Accordingly, the sensory perception of the composite wave in each of the respective frequency ranges are different from one another. Additionally, it is also confirmed that the causes for the formation of the waves are different from each other in accordance with the frequencies. Therefore, in order to evaluate the result of the coated paint film and to feedback the result to a production process of automotive vehicles, it is necessary to independently quantify the degrees of unevenesses having a variety of ranges of frequencies.

Known systems for evaluating the unevenness of the surface of a coated paint film or the like are arranged to make measurement upon contact with the surface of the coated paint film. Accordingly, employing such evaluating systems renders impossible an evaluation of the paint film coated on a surface having a variety of curvatures such as a vehicle body panel, and also renders impossible an automatic inspection for the coated paint film in a production process of the automotive vehicles. Additionally, in any of the above conventional evaluating systems, it is impossible to obtain a broad field of view for evaluation, so that there arises a scattering in evaluation values, while also making detection of unevenness in the order of several cm impossible.

In order to solve the above problems, methods for quantifying the gloss and brightness character of a coated paint film are disclosed in Japanese Patent Provisional Publication Nos. 58-97608 and 61-217708. In these methods, a rectangular pattern is projected onto the surface of a coated paint film. The reflected light of the projected pattern is received by a one-dimensional photoelectric element. The diffusion condition of the reflected light is quantified by using a power spectrum upon a Fourier transform. In addition, it has recently been proposed to process a two-dimensional image as disclosed in Japanese Patent Provisional Publication Nos. 1-210806, 1-210807 and 1-213509.

However, difficulties have been encountered in the above conventional systems and methods for evaluating the gloss and brightness character of the coated paint film, in which a mechanism for detecting and analyzing the surface condition of the coated paint film is considerably different from that based on human's visual observation, so that resulting evaluation values are not in correlation to those based on the human's visual observation. Additionally, it is difficult to measure or evaluate the gloss and brightness character when the surface of coated paint film has a relatively large curvature, for example, in case of the paint film coated on a vehicle body. Furthermore, it has been also problematic that the resulting evaluation values are unavoidably scattered in a wide region, even in measurements or evaluations in the same condition. Thus, the above-discussed conventional systems and methods for evaluating the gloss and brightness character of the coated paint film are problematic from the practical view points.

SUMMARY OF THE INVENTION

It is an object of the present invention to provide an improved method for evaluating gloss and brightness character of a coated paint film, which overcomes the drawbacks encountered in the corresponding conventional methods.

Another object of the present invention is to provide an improved method for evaluating the gloss and brightness character of a coated paint film, in which the mechanism for detecting and analyzing the surface condition of a coated paint film is similar to that based on human's visual observation.

A further object of the present invention is to provide an improved method for evaluating the gloss and brightness character of a coated paint film, in which the resulting evaluation values are in close correlation to those based on a human's visual observation.

The method for evaluating the gloss and brightness character of a coated paint film according to the present invention comprises the steps of projecting a brightness and darkness pattern onto the surface of the coated paint film; converting the projected pattern into a two-dimensional brightness and darkness pattern; separating the disturbance of the two-dimensional brightness and darkness pattern into a plurality of spatial frequency ranges; and quantifying independently each of the spatial frequency ranges.

With the above method, image information data corresponding to the unevenness of the surface of the coated paint film are separated into a plurality of spatial frequency ranges. The spatial frequency ranges are respectively independently quantified thereby to evaluate the gloss and brightness character of the coated paint film. Accordingly, such an evolution is accomplished under a condition close to that based on a human's visual observation. The reasons therefor are believed to be as follows:

A coated paint film is felt to have at least three appearances in accordance with spatial frequencies of on unevenness of the surface thereof. A first spatial frequency range (represented in wavelength) not larger than about 0.1 mm is perceived as a so-called gloss feeling. A second spatial frequency range (represented in wavelength) between about 0.1 mm and about 1 mm is perceived as a so-called thickness feeling. A third spatial frequency range (represented in wavelength) between about 1 mm and several 10 mm is perceived as a so-called smoothness (orange skin-like) feeling. Within the third spatial frequency range, a frequency part (represented in wavelength) over about 10 mm corresponds to undulation of the coated paint film surface and may be removed from the smoothness feeling because the undulation does not exhibit such an unpleasant a feeling as to degrade the quality of a product. In this connection, these spatial frequency ranges corresponding to the above respective perceptions may shift slightly in accordance with evaluators, evaluation conditions (for example, a distance between the evaluator and the coated paint film), so that there arises an overlap between the adjacent spatial frequency ranges; however, the independence of each spatial frequency range cannot be removed. The respective spatial frequency ranges mentioned above are commonly defined values. Thus, according to the present invention, the gloss and brightness character is evaluated upon all the quantified evaluation values corresponding to the respective sensory perceptions, so that the evaluation can be achieved in a condition close to that based on a human's visual observation.

DETAILED DESCRIPTION OF THE INVENTION

Figure 1:
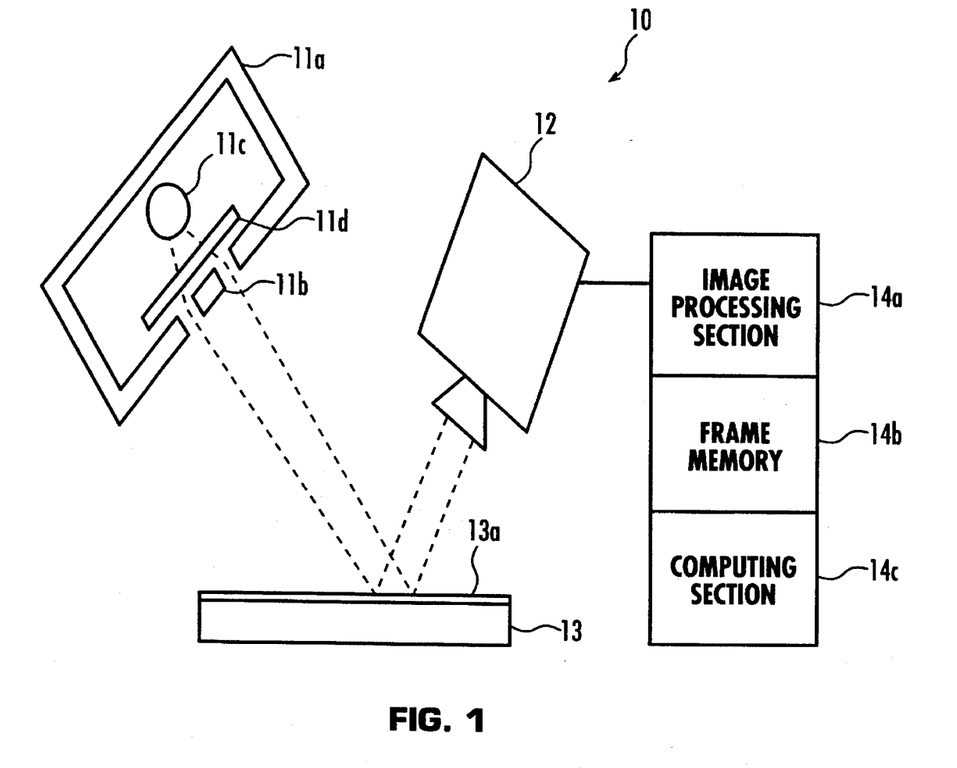
FIG. 1 is a schematic view of an example of a system for accomplishing a method for evaluating the gloss and brightness of a coated paint film, in accordance with the present invention.

Referring now to FIG. 1 of the drawings, there is shown an example of a system 10 for evaluating or measuring a gloss and brightness character of a coated paint film, according to a method of the present invention. The measuring system 10 includes a light source box 11a in which a light source 11c is disposed. Light from the light source 11c is homogeneously diffused in the box 11a and passes through a diffusion plate 11d disposed in the box 11a. The light passed through the diffusion plate 11d then passes through slits 11b, so that a slit light (or a brightness and darkness pattern) having a uniform brightness is radiated onto the surface of a coated paint film 13a formed on a sheet or plate 13 at a predetermined entry angle (not identified). The thus radiated slit light is reflected on the surface of the coated paint film 13a and enters a CCD (charge-coupled device) camera 12 which takes therein the reflected light as a map (image informations) on the surface of the coated paint film 13a. The image information taken in the CCD camera is supplied to an image processing device 14. The image processing device 14 includes an image processing section 14a to which the image information from the CCD camera 12 are input. In the processing section 14a, the image information of one frame is converted into digital informations by an A/D conversion. The digital information includes 512×512 imaging elements each of which includes 256 brightness (or darkness) tones. One imaging element corresponds to one bite. The digital information is then stored in a frame memory 14b and supplied to a computing section 14c. In the computing section 14c, the digital informations or data from the frame memory 14b are quantified for respective spatial frequency ranges, in accordance with a method later discussed in detail.

An embodiment of an evaluating or measuring method for the gloss and brightness character of the coated paint film 13a on the sheet (for example, a steel sheet of an automotive vehicle body) will be discussed hereinafter.

Figure 2:
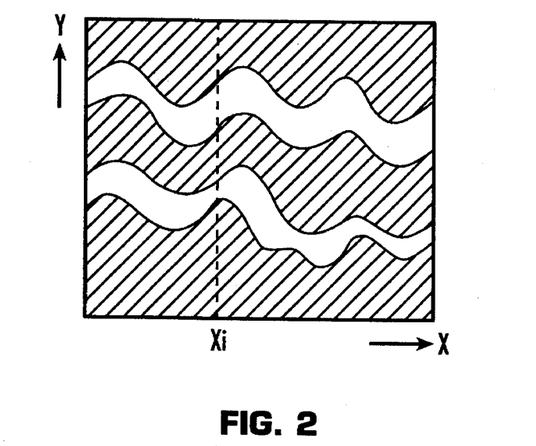
FIG. 2 is an illustration showing an example of an image taken in an image processing device of the system of FIG. 1.

FIG. 2 shows an example of the map of an original image (image information) picked up by the CCD camera 12. The map is a two dimentional brightness and darkness image or pattern and has a visual field of 50 mm×50 mm. The visual field is divided into 512×512 imaging elements, so that each imaging element exprsses the image information of about 0.1 mm. As seen from FIG. 2, the straight slit light radiated onto the surface of the coated paint film 13a is warped or disturbed in a certain frequency in accordance with the unevenness of the coated paint film surface.

According to this evaluation method, first the warp or disturbance of the slit light in the image information data of the map of FIG. 2 are separated corresponding to a plurality of spatial frequency ranges. Then, the image information of the warp is quantified for the respective spatial frequency ranges. In this evaluation method, a smoothing processing is applied as a band pass filter for the spatial frequencies, in which the spatial frequencies are separated into a plurality of ranges. The thus processed image informations of the warp is finally numerically expressed. The above evaluation method will be explained with reference to a flowchart of FIG. 3.

Figure 3:
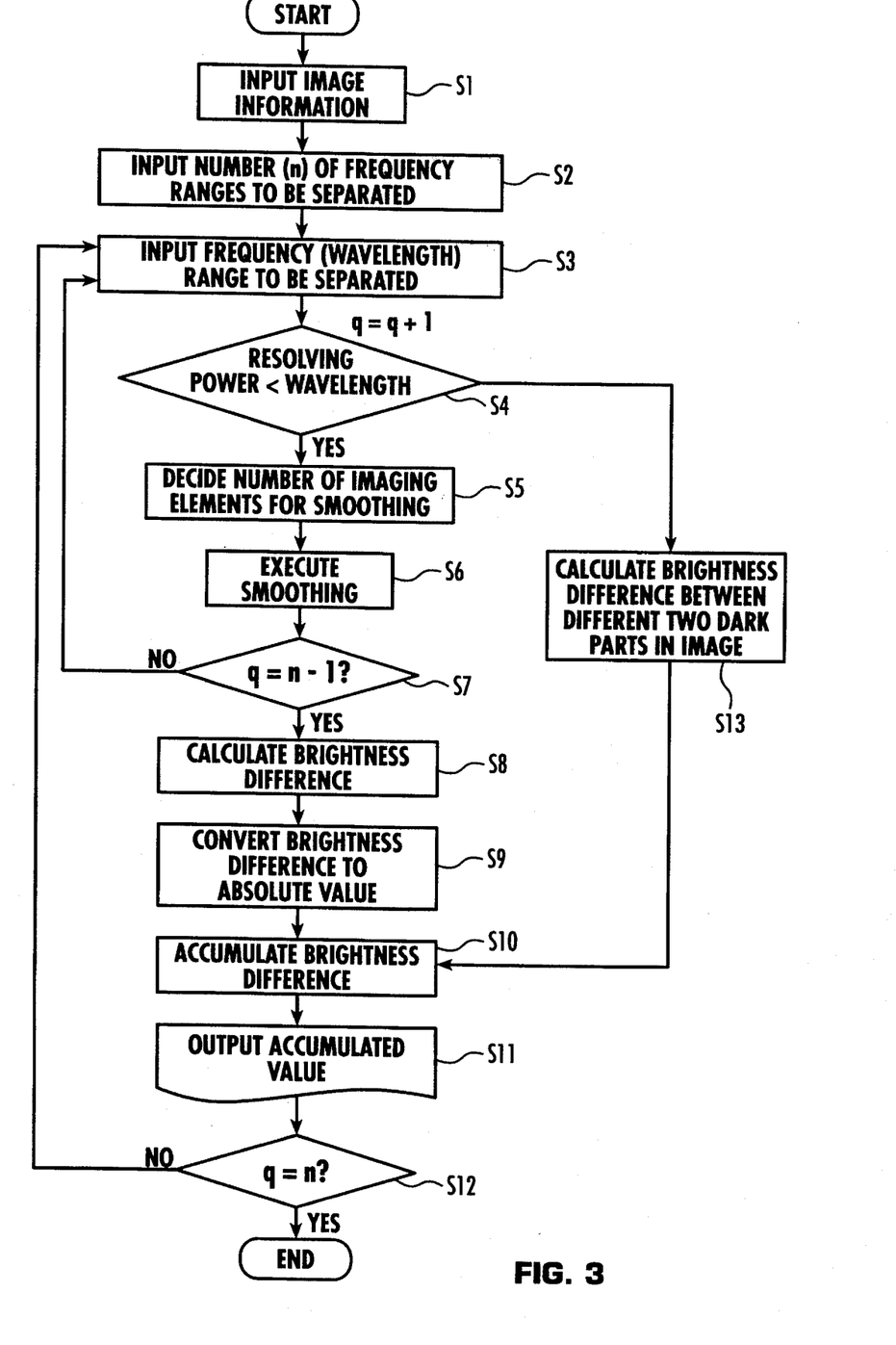
FIG. 3 is a flowchart showing an example of processing the image taken in the image processing device, in accordance with the priciple of the present invention.

In the flowchart of FIG. 3, at a step S1, the data of the image information (picked up by the CCD camera 12) corresponding to the image as shown in FIG. 2 are input to the image processing device 14. The data include image information of 512 (imaging elements)×512 (imaging elements)×256 (tones). At a step S2, a number (n) of spatial frequency ranges of the wave shapes of the warp in the map of FIG. 2 is appointed and input to the image processing device 14, the frequency ranges being separated from each other. In this case, there are four spatial frequency ranges which respectively correspond to four texture feelings of the coated paint film 13a, i.e., an undulation of the coated paint film surface or a curvature of the sheet (or an article) coated with the paint film, a smoothness feeling, a thickness feeling, and a gloss feeling. Thus, although the number of the spatial frequency ranges seems to be four, the spatial frequency range corresponding to the undulation and the curvature does not have a correlation to the quality of the coated paint film. It is only used as a measure for obtaining the smoothness, thickness and gloss feelings without being quantified. Accordingly, the actual number (n) of the spatial frequency ranges to be input is three corresponding to the smoothness, thickness and gloss feelings.

At a step S3, the respective spatial frequency ranges are appointed and input to the image processing device 14. In this instance, the frequency range corresponding to the undulation or the curvature is larger than that corresponding to a wavelength of 10 mm. The frequency range corresponding to the smoothness feeling is between a frequency corresponding to a wavelength of 10 mm and a frequency corresponding to a wavelength larger than 1.0 mm. The frequency range corresponding to the thickness feeling is between a frequency corresponding to the wavelength of 1.0 mm and a frequency corresponding to the wavelength larger than 0.1 mm. The frequency range corresponding to the gloss feeling is smaller than a frequency corresponding to a wavelength of 0.1 mm. The reference character q at the step S3 in FIG. 3 denotes the number of times of inputting the spacial frequency range.

At a step S4, if the wavelength serving as a border between the adjacent spatial frequency ranges is larger than a resolving power (the field of view÷512), a flow goes to a step S5 to process the image information data of the undulation or the curvature, the smoothness feeling and the thickness feeling. If the same wavelength is smaller than the resolving power, the flow goes to a step S13 to process the image information data of the gloss feeling. Since the resolving power of the image information data in this instance is about 0.1 mm, the gloss feeling having a wavelength component smaller than 0.1 mm is out of the resolving power and therefore cannot be processed unless the field of view is changed (enlarged) or, otherwise, another algorithm is used.

At a step S5, a number of imaging elements for smoothing is decided. In other words, the size of a mask for smoothing is set to cut a higher frequency (small wavelength) side relative to the frequency range to be separated. At a step S6, the whole frame is smoothed upon moving the mask. At a step S7, the flow including the steps S3 to S6 is repeated by the number (n) of the frequency ranges to be separated. At a step S8, a brightness difference between the high frequency side-cut image and the original image is calculated upon subtraction between the two images. At a step S9, the difference is converted to its absolute value by cancelling + and −, since only the magnitude of the difference is important. At a step S10, all the differences between the two images are accumulated. At a step S11, an accumulated value obtained at the step S10 is output as an evaluation value. At a step S12, the flow including the steps S3 to S11 is repeated by the number (n) of the frequency ranges to be separated. At a step S13, a parameter is obtained by calculating the difference between a dark part and a bright part in the original image since the gloss feeling has the wavelength component smaller than the resolving power. More specifically, the difference in brightness between the dark part near the bright part and the dark part sufficiently far from the bright part is measured. The thus obtained brightness difference is accumulated at the step S10.

Here, separation of the spatial frequency ranges upon the smoothing as shown at steps 5 to 10 will be discussed further in detail.

First, the image (the undulation and curvature) having a wavelength component larger than 10 mm is defined. In FIG. 2, the coordinates of the imaging element are set as (Xi, Yj) where i=0, 1, 2, . . . , 511, and j=0, 1, 2, . . . , 511. The brightness of the imaging element is set as Zij. For definition of the undulation and curvature image, wavelengths not larger than 10 mm are cancelled, in which the value of Zij is newly defined as an average value of ±50 imaging elements (each represented by the reference character p) in the horizontal direction or the direction of x-axis in FIG. 2 thereby obtaining $Z^*ij$ shown in an equation (1) within a range of $50 \leq i \leq 461$:

$$Z^*ij = \sum_{i=p-50}^{p+50} Zij/101 \quad (p = 50 \text{ to } 461) \quad (1)$$

Next, for defining the image (in connection with the smoothness feeling) having a wavelength component not larger than 10 mm and larger than 1.0 mm, the wavelengths not larger than 1.0 mm are cancelled, in which the value of Zij is newly defined as an average value of ±5 imaging elements in the horizontal direction or the x-axis direction in FIG. 2 thereby obtaining $Z^{**}ij$ shown in an equation (2) within a range of $5 \leq i \leq 506$:

$$Z^{**}ij = \sum_{i=p-5}^{p+5} Zij/11 \quad (p = 5 \text{ to } 506) \quad (2)$$

The thus newly defined $Z^*ij$ and $Z^{**}ij$ are memorized in a frame memory other than that for the infornation of the original image. In accordance with the memorized $Z^*ij$ and $Z^{**}ij$, the warps (wave forms) or disturbance of the image in connection with the smoothness feeling and the thickness feeling are represented as tone changes in equations (3) and (4):

Smoothness feeling: $Zhij=Z^{**}ij-Z^*ij$ (3)

Thickness feeling: $Znij=Zij-Z^*ij$ (4)

In this instance, all the image information corrsponding to the wave forms (in connection with the smoothness and thickness feelings) of the image in FIG. 2 are accumulated as absolute values in the whole field of view thereby to be quantified by the following equations (5) and (6):

Smoothness feeling: $Th=\Sigma\Sigma|Zhij|$ (5)

Thickness feeling: $Tn=\Sigma\Sigma|Znij|$ (6)

Although the above smoothing has been described as being accomplished only in the horizontal direction of x-axis in FIG. 2, it will be understood that such smoothing may be accomplished only in the vertical direction or the direction of the y-axis, or both in the horizontal and vertical directions by using windows in the respective directions. In such smoothing, if the accuracy of separation of the wavelength (frequency) components is not high, a two-dimentional smoothing with a window is effective while a considerable time is required.

While only the smoothing has been shown and described as being made to obtain the quantified values of the equations (5) and (6), it will be appreciated that the following processing may be accomplished for the same purpose: Filtering with a desired frequency is made on an image after being processed by a two-dimensional FFT (fast Fourier transform), and then the image after filtering is processed by a reverse FFT thereby to define a new two-dimensional image.

Subsequently, quantifying the gloss feeling, or perception, at the steps 4, 13 and 10 of FIG. 3 will be explained in further detail with reference to FIG. 4. Since the gloss perception results from a spatial frequency component not larger than 0.1 mm in wavelength, the resolving power is insufficient with the field of view used in the above discussed processing. It is, of course, possible to enlarge the field of view by using a closing-up technique or the like so as to separate the spatial frequency component in the same manner as that discussed above. However, this will complicate an optical system of the measuring system, requiring a high accuracy in setting the focal distance and the like. Accordingly, in this instance, a further practical technique is employed which uses the picked-up image of FIG. 2 as it is, with the same field of view as in the above-discussed processing. This technique makes it possible to quantify the gloss feeling with an algorithm similar to that by which a human evaluates the gloss feeling.

Figure 4:
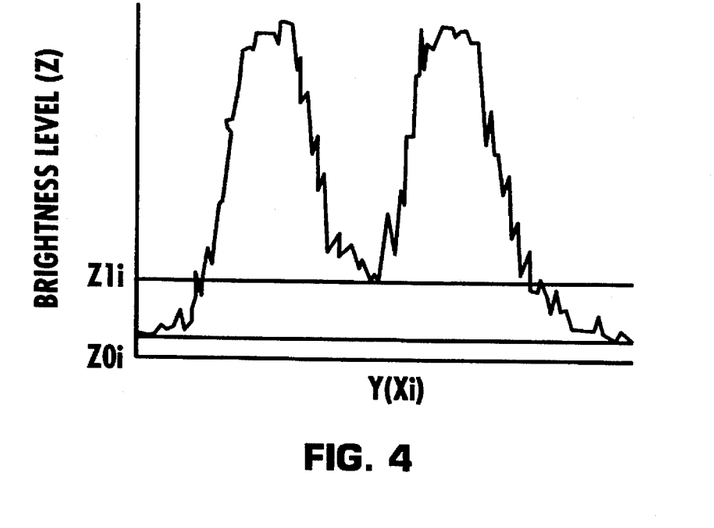
FIG. 4 is a graph to be used for quantifying a so-called gloss feeling of the coated paint film, in the processing of FIG. 3.

First, a brightness level Z is extracted at a point xi of the x-axis and along the direction of the y-axis, as shown in FIG. 4. In case the brightness feeling is low, diffusion of light occurs owing to the uneveness (small in wavelengh) of the surface of the coated paint film. This results in a phenomena that the brightness value at a dark part (hatched part in FIG. 2) near a bright part (not-hatched part in FIG. 2) cannot be lowered sufficiently as compared with another dark part (hatched part in FIG. 2) sufficiently far from the bright part. This phenomena will be defined by using FIG. 4. In FIG. 4, the brightness value of the dark part sufficiently far from the bright part is Z0i; and the brightness value of the center of the dark part between the bright parts is Z1i. The gloss feeling can be obtained from the difference between the brightness values Z0i and Z1i. Thus, in this instance, the gloss feeing is defined by the following equation (7).

Gloss feeing: $Tt=\Sigma(Z1i-Z0i)$ (7)

Figure 5A:
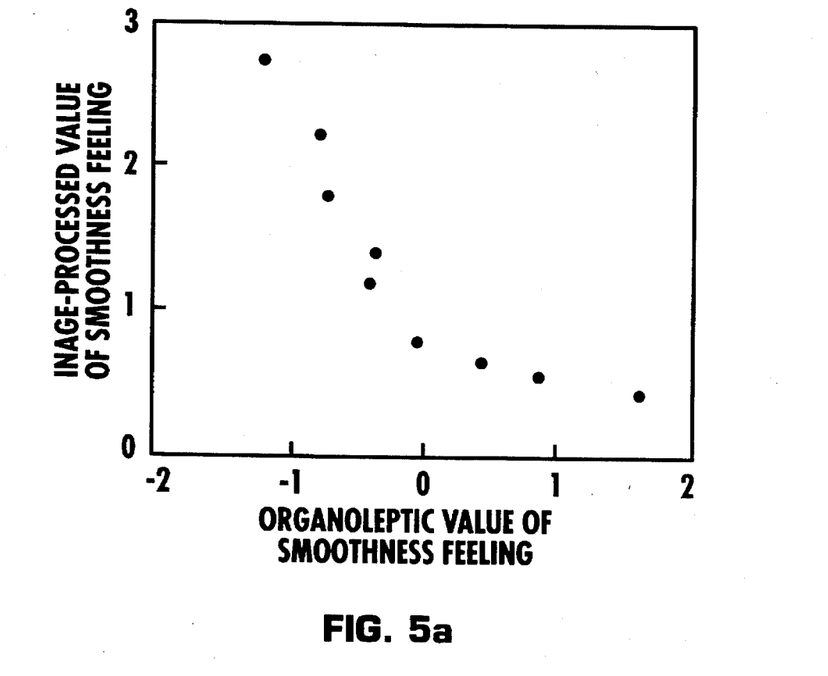
FIG. 5A is a graph showing the correlation between an image-processed value and an organoleptic value in terms of a so-called smooth feeling of the coated paint film.
Figure 5B:
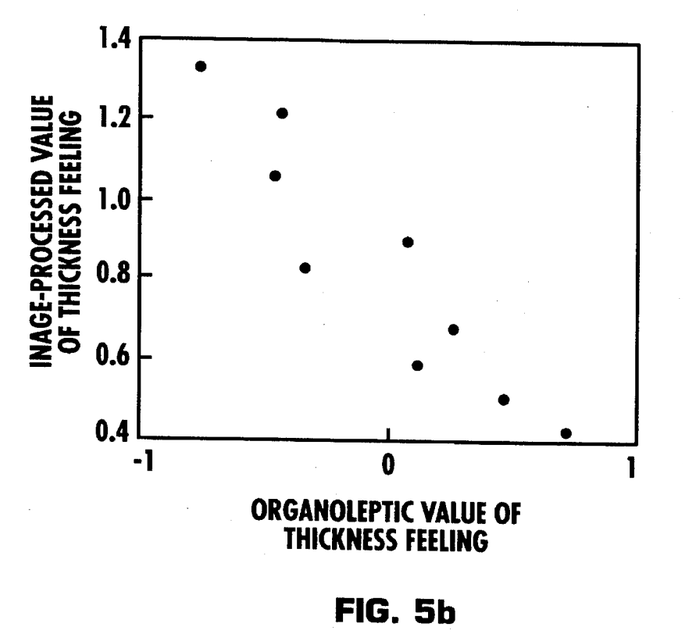
FIG. 5B is a graph similar to FIG. 5A but in terms of a so-called thickness feeling.
Figure 5C:
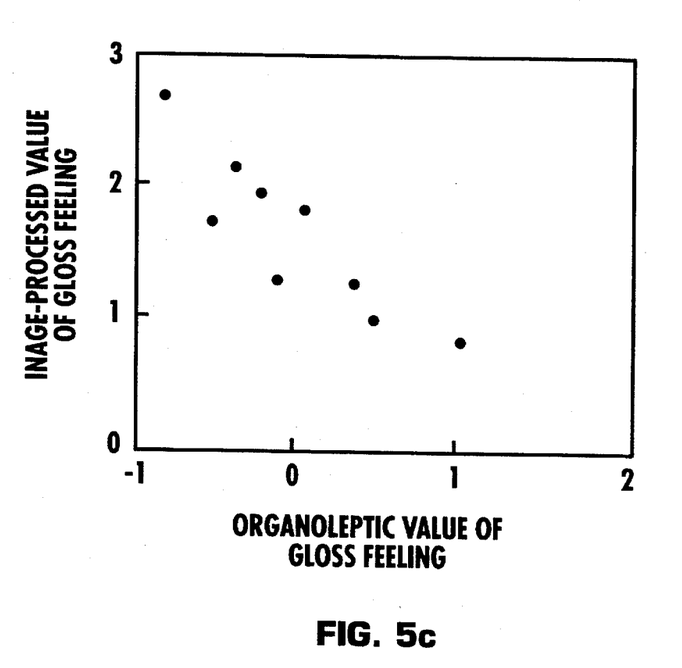
FIG. 5C is a graph similar to FIG. 5A but in terms of the gloss feeing of the coated paint film.

In order to confirm correlation or agreement of the smoothness, thickness and gloss feelings Th, Tn, Tt quantified by the above discussed manner with organoleptic evaluation of such feelings, experiments were conducted by which the results of FIGS. 5A to 5C were obtained. In the experiments, nine specimens were prepared by coating paint films on a respective nine set of steel sheets, in which the surface conditions of the coated paint films were variously changed. On the thus prepared specimens, the evaluation of the method according to the present invention is made to obtain an image-processed value or the evaluation value, and the organoleptic evaluation was made to obtain an organoleptic value. The results of the evaluations for the smooth feeling, the thickness feeling and the gloss feeling are shown in FIGS. 5A, 5B and 5C, respectively. It will be seen from FIGS. 5A, 5B and 5C, that there is a close correlation between the image-processed value and the organoleptic value.

Thus, according to the above-discussed evaluating method of the present invention, the gloss and brightness character of the coated paint film can be automatically evaluated in a sense close to a human's actual feeling, by accomplishing a total quantification based on the quantified feelings Th, Tn, Tt.

Having described a specific embodiment of the gloss and brightness character evaluation method of the present invention, it is believed that modification and variation of the invention is possible in light of the above teachings. For example, it will be understood that in the above discussed embodiment, spatial frequency ranges other than those mentioned above may be extracted by changing the field of view of the image taken in the image processing device 14. Accordingly, application of this treatment can set an evaluation value corresponding to a factor by which a failure in paint film coating is made. For example, failed orientation of aluminum flake in a metallic paint can be evaluated upon being extracted from the smoothness feeling of the coated paint film.

As discussed above, according to the present invention, the brightness and darkness pattern projected on the surface of the coated paint film is picked up and taken in the image processing device. Disturbance of the taken-up pattern is separated into a plurality of spatial frequency ranges. Each of the spatial frequency ranges is quantified thereby to evaluate the gloss and brightness character of the coated paint film. Accordingly, evaluation results in close agreement with human senses can be obtained instantly and without mechanical contact with the coated paint film.

In case of applying the gloss and brightness character evaluating method of the present invention onto a production line of automotive vehicles, paint films having a variety of colors and coated on a variety of shapes of vehicle bodies are objects to be measured for evaluation. More specifically, the feature of the above-discussed embodiment resides in the fact that a plurality of processed images are formed on the basis of the projected pattern, upon which the difference in brightness level is calculated between the processed images thereby obtaining an evaluation value. Accordingly, in this embodiment, a correction for difference in colors (for example, correction for binary levels) is unnecessary. Additionally, the above-discussed embodiment of the present invention can be effectively applied for evaluation of the gloss and brightness character of the paint film coated on a vehicle body surface having a variety of curvatures, upon removing a spatial frequency component corresponding to the curved paint film surfaces. This makes possible an on-line measurement of the gloss and brightness character of the coated paint film in a painting line for the automotive vehicles, which has hetherto been difficult by the conventional methods and systems.

What is claimed is:

1. A method for evaluating a gloss and brightness character of a coated paint film, comprising the following steps:

projecting a brightness and darkness pattern, said pattern extending along a first direction and alternating between brightness and darkness along a second direction perpendicular to said first direction, onto a surface of the coated paint film;

converting the projected pattern into a two-dimensional brightness and darkness pattern;

separating a disturbance of the two-dimensional brightness and darkness pattern into a plurality of predetermined spatial frequency ranges of said disturbance, at least one spatial frequency of said disturbance within at least one of said ranges having a propagation axis along said first direction, each of said predetermined spatial frequency ranges being a range within which a total energy correlates to a human perception of one of a plurality of gloss and brightness characters of the coated paint film;

quantifying a total energy for a first range from among said plurality of predetermined spatial frequency ranges;

generating a first estimate, in accordance with said quantified total energy for said first range, said first estimate corresponding to a predetermined human perception associated with a value of said quantified total energy for said first range, of at least a first characteristic from among said plurality of gloss and brightness characteristics;

quantifying a total energy for a second range from among said plurality of predetermined spatial frequency ranges;

generating an estimate, in accordance with said quantified total energy for said second range, said estimate corresponding to a predetermined human perception associated with a value of said quantified total energy for said second range, of at least a second characteristic from among said plurality of gloss and brightness characteristics.

2. A method as claimed in claim 1, wherein the disturbance separating step includes smoothing each of the spatial frequency ranges of the two-dimensional brightness and darkness pattern, said smoothing using an averaging filter with an averaging distance corresponding to the frequency range.

3. A method as claimed in claim 1, wherein said disturbance separating step includes filtering each of the spatial frequency ranges of the two-dimensional brightness and darkness pattern after a fast Fourier transform.

4. A method as claimed in claim 1, wherein the converting step is carried out to form a first image having the two-dimensional brightness and darkness pattern, wherein the disturbance separating step is carried out to form a plurality of second images corresponding to the pattern, each of said second images being a spatial filtered image corresponding to one of said spatial frequency ranges.

5. A method as claimed in claim 4, wherein said quantifying is carried out in accordance with a difference in brightness between a plurality of the images which are subjected respectively to different processings and both based on the projected brightness and darkness pattern.

6. A method as claimed in claim 5, said quantifying is carried out in accordance with a difference in brightness between the first image and each of the second images.

7. A method as claimed in claim 4, wherein said quantifying is carried out in accordance with a difference in brightness level between a first dark part near a bright part and a second dark part far from the bright part in the first image, in quantifying one of the spatial frequency range less than a resolving power for the processed image.

8. A method as claimed in claim 1, wherein the projecting pattern converting step includes picking up the projected pattern by a CCD camera to form the two-dimensional pattern.

9. A method as claimed in claim 1, wherein the human perceptions include a smoothness feeling, a thickness feeling and a gloss perception.

10. A method as claimed in claim 9, wherein said smoothness, thickness and gloss feelings respectively correspond to first, second and third spacial frequency, said second wavelength regions having a center frequency lower in wavelength than a center frequency of said first wavelength region and higher in wavelength than a center frequency of said third wavelength region.

11. A method as claimed in claim 10, wherein said first wavelength region is not lower in wavelength than 1 mm, said second wavelength region is lower in wavelength than 1 mm and higher in wavelength than 0.1 mm, and a third wavelength region is not higher in wavelength than 0.1 mm.

12. A method for evaluating a gloss and brightness character of a paint film coated on a vehicle body surface having curvatures, said method comprising the following steps:

projecting a brightness and darkness pattern onto a surface of the coated paint film, said pattern extending along a first direction and alternating between brightness and darkness along a second direction perpendicular to said first direction;

converting the projected pattern into a two-dimensional brightness and darkness pattern;

separating a disturbance of the two-dimensional brightness and darkness pattern into a plurality of predetermined spatial frequency ranges of said disturbance, at least one spatial frequency of said disturbance within at least one of said ranges having a propagation axis along said first direction, each of said predetermined spatial frequency ranges being a range within which a total energy correlates to a human perception of one of a plurality of gloss and brightness character of the coated paint film;

quantifying a total energy for a first range from among said plurality of predetermined spatial frequency ranges;

generating a first estimate, in accordance with said quantified total energy for said first range, said first estimate corresponding to a predetermined human perception associated with a value of said quantified total energy for said first range, of at least a first character from among said plurality of gloss and brightness characters;

quantifying a total energy for a second range from among said plurality of predetermined spatial frequency ranges; and generating an estimate, in accordance with said quantified energy for said second range, said estimate corresponding to a predetermined human perception associated with a value of said quantified total energy for said second range, of at least a second characteristics from among said plurality of gloss and brightness characters.

* * * * *

UNITED STATES PATENT AND TRADEMARK OFFICE
CERTIFICATE OF CORRECTION

PATENT NO. : 5,550,632

DATED : August 27, 1996

INVENTOR(S) : Hiroaki Harata

It is certified that error appears in the above-identified patent and that said Letters Patent is hereby corrected as shown below:

On title page, item [73]
insert --Assignee: Nissan Motor Co., Ltd., Yokohama City, Japan--.

Signed and Sealed this

Twenty-fourth Day of June, 1997

Attest:

BRUCE LEHMAN

Attesting Officer

Commissioner of Patents and Trademarks